US009804097B1

(12) United States Patent
Tang et al.

(10) Patent No.: US 9,804,097 B1
(45) Date of Patent: Oct. 31, 2017

(54) CROP STAND ANALYZER USING REFLECTIVE LASER PROXIMITY SENSORS

(71) Applicant: Iowa State University Research Foundation, Inc., Ames, IA (US)

(72) Inventors: Lie Tang, Ames, IA (US); Ji Li, Ames, IA (US); Yin Bao, Ames, IA (US); Jian Jin, Johnston, IA (US); Akash Dev Nakarmi, Ames, IA (US)

(73) Assignee: Iowa State University Research Foundation, Inc., Ames, IA (US)

(*) Notice: Subject to any disclaimer, the term of this patent is extended or adjusted under 35 U.S.C. 154(b) by 345 days.

(21) Appl. No.: 14/717,613

(22) Filed: May 20, 2015

Related U.S. Application Data

(60) Provisional application No. 62/006,301, filed on Jun. 2, 2014.

(51) Int. Cl.
*G01N 21/84* (2006.01)

(52) U.S. Cl.
CPC ..... *G01N 21/84* (2013.01); *G01N 2021/8466* (2013.01); *G01N 2201/021* (2013.01); *G01N 2201/06113* (2013.01)

(58) Field of Classification Search
CPC ............... G01N 21/84; G01N 2021/8466
See application file for complete search history.

(56) References Cited

U.S. PATENT DOCUMENTS

| 4,768,713 | A  | * | 9/1988  | Roper    | B05B 9/06   |
|           |    |   |         |          | 236/77      |
| 4,989,783 | A  | * | 2/1991  | Douglas  | B05B 12/122 |
|           |    |   |         |          | 239/105     |
| 5,144,767 | A  | * | 9/1992  | McCloy   | B05B 12/12  |
|           |    |   |         |          | 47/1.7      |
| 5,373,057 | A  | * | 12/1994 | Watanabe | C08L 67/02  |
|           |    |   |         |          | 525/166     |
| 5,585,626 | A  | * | 12/1996 | Beck     | G01J 1/04   |
|           |    |   |         |          | 250/222.1   |
| 5,789,741 | A  | * | 8/1998  | Kinter   | G01J 3/10   |
|           |    |   |         |          | 209/582     |
| 6,073,427 | A  |   | 6/2000  | Nichols  |             |
| 6,596,996 | B1 | * | 7/2003  | Stone    | G01J 3/427  |
|           |    |   |         |          | 250/341.1   |
| 6,919,959 | B2 | * | 7/2005  | Masten   | A01M 7/0089 |
|           |    |   |         |          | 356/328     |
| 7,362,439 | B2 | * | 4/2008  | Franzen  | A01D 34/006 |
|           |    |   |         |          | 356/445     |
| 7,412,330 | B2 |   | 8/2008  | Spicer et al. |        |

(Continued)

FOREIGN PATENT DOCUMENTS

EP 1777486 4/2007
WO WO 2016025848 A1 * 2/2016 ........... A01B 79/005

*Primary Examiner* — Charlie Y Peng
(74) *Attorney, Agent, or Firm* — McKee, Voorhees & Sease, PLC (57) ABSTRACT

A crop stand analyzer includes a first plurality of reflective laser proximity sensors, the reflective laser proximity sensors arranged in a vertical row and perpendicularly to a ground surface to detect plant objects, a distance sensor, and a processor operatively connected to the first plurality of reflective laser proximity sensors and the distance sensor. The crop stand analyzer is configured to generate side-view profiles for the plant objects and then extract plant stand information via these profiles.

17 Claims, 12 Drawing Sheets

(56) References Cited

U.S. PATENT DOCUMENTS

| | | | |
|---|---|---|---|
| 7,848,865 B2 * | 12/2010 | Di Federico | A01B 79/005 |
| | | | 701/50 |
| 9,417,120 B2 * | 8/2016 | Zielke | G01J 1/0403 |
| 9,629,313 B1 * | 4/2017 | Grossman | A01G 25/16 |
| 2002/0011567 A1 * | 1/2002 | Ozanich | G01J 3/02 |
| | | | 250/326 |
| 2014/0259920 A1 * | 9/2014 | Wilson | A01G 31/02 |
| | | | 47/62 R |
| 2014/0283442 A1 * | 9/2014 | Thomas, III | A01G 7/06 |
| | | | 47/1.5 |
| 2016/0106038 A1 * | 4/2016 | Boyd | A01D 41/141 |
| | | | 56/10.4 |
| 2016/0198639 A1 * | 7/2016 | Millar | A01G 7/045 |
| | | | 315/152 |
| 2017/0032258 A1 * | 2/2017 | Miresmailli | A01G 7/00 |
| 2017/0105358 A1 * | 4/2017 | Wilson | A01G 7/045 |

* cited by examiner

CROP STAND ANALYZER USING REFLECTIVE LASER PROXIMITY SENSORS

PRIORITY STATEMENT

This application claims priority under 35 U.S.C. §119 to provisional application Ser. No. 62/006,301, filed Jun. 2, 2014, which is herein incorporated by reference in its entirety.

GRANT REFERENCE

This invention was made with government support under Grant No. 2012-67009-19713 awarded by USDA/NIFA. The government has certain rights in the invention.

FIELD OF THE INVENTION

The present invention relates to real-time in-field crop sensing. More particularly, but not exclusively, it relates to a sensing system configured to automatically acquire crop stand information such as crop stand location, stem size, crop population, and interplant spacing in field and in real-time.

BACKGROUND OF THE INVENTION

Obtaining crop population data at a large scale is critical to plant breeders and plant scientists. In addition, reliably detecting crop stand in-field and in real-time can enable a range of precision agriculture applications and lead to new inventions in agricultural field automation such as robotic weed control. What are needed are new and improved methods, systems, and apparatuses for obtaining crop population data.

SUMMARY OF THE INVENTION

Therefore, it is a primary object feature, or advantage of the present invention to improve over the state of the art.

It is a further object, feature, or advantage to use reflective laser proximity sensors with background suppression and adjustable cutoff range.

It is a still further object, feature, or advantage to use vertically lined up sensor banks with adjustable sensor positions.

Another object, feature, or advantage is to register sensor signals with a high-resolution distance signal.

Yet another object, feature, or advantage is to place sensors at different heights to accommodate different growth stages of crops.

A further object, feature, or advantage of the present invention is to use one sensor bank to sense one crop row from only one side of a crop row.

A still further object, feature, or advantage of the present invention is to use multistate scanning for stem detection.

Another object, feature, or advantage of the present invention is to measure plant spacing and stem diameter along with plant population.

Yet another object, feature, or advantage of the present invention is to deliver real-time information for high speed field operation.

A further object, feature, or advantage of the present invention is to provide for in-field plant phenotyping for plant breeders, agronomists, and plant geneticists.

A still further object, feature, or advantage of the present invention is to provide for data collection as a part of crop scouting for field specialists and farmers.

Another object, feature, or advantage is to provide for interplant spacing data collection for planter manufacturers to conduct field validation of seed metering systems.

Yet another object, feature, or advantage is to provide for plant population data collection for crop growers.

A further object, feature, or advantage to provide a plant population sensor that can be mounted on all-terrain vehicles, tractors, sprayers, harvesters, or other equipment.

A still further object, feature, or advantage to generate population data that can be incorporated into yield data maps for crop management such as replanting, variable seeding, and fertilization.

Another object, feature, or advantage is to provide a crop plant recognition sensor that is insensitive to outdoor lighting conditions and can be used in precision weeding and variable rate fertilizer applications.

One or more of these and/or other objects, features, or advantages will become apparent from the Specification and claims that follow. No single embodiment need exhibit each or every object, feature, or advantage. Different embodiments may have different objects, features, or advantages. The present invention is not to be limited by or to the objects, features, or advantages listed herein.

According to one aspect, a crop stand analyzer is provided. The crop stand analyzer includes a first plurality of reflective laser proximity sensors, the reflective laser proximity sensors arranged in a vertical row and generally perpendicularly (it need not be exactly perpendicular) to a ground surface to detect plant objects, a distance sensor and a processor operatively connected to the first plurality of reflective laser proximity sensors and the distance sensor. The crop stand analyzer is configured to generate side-view profiles for the plant objects and then extract plant stand information via these profiles.

According to another aspect, a method for analyzing crop stands is provided. The method includes providing a system having (a) a first plurality of reflective laser proximity sensors, the reflective laser proximity sensors arranged in a vertical row and perpendicularly to a ground surface to detect plant objects, (b) a distance sensor, and (c) a processor operatively connected to the first plurality of reflective laser proximity sensors and the distance sensor. The method further includes acquiring laser data from the first plurality of reflective laser proximity sensors, acquiring position data from the distance sensor, registering the position data with the laser data using the processor, and computing plant data comprising at least one of plant population data, interplant spacing, and stem spacing from the position data and the laser data. One or more of the steps of the method may be performed as the system is moved through a field. The method may further include making plant breeding or commercialization decisions based on the plant data.

According to another aspect, a crop stand analyzer includes a plurality of row units wherein each of the row units comprises (a) a first plurality of reflective laser proximity sensors, the reflective laser proximity sensors arranged in a vertical row and perpendicularly to a ground surface to detect plant objects, (b) a distance sensor. The crop stand analyzer further includes a processor operatively connected to each of the first plurality of reflective laser proximity sensors and each of the distance sensors. The processor may be configured to generate side-view profiles for the plant objects and then extract plant stand information via these profiles. The crop stand analyzer may further include a mobile platform, each of the first plurality of reflective laser proximity sensors mounted to the mobile platform and at least one wheel operatively connected to the mobile platform.

DETAILED DESCRIPTION

Obtaining crop population data at a large scale is critical to plant breeders and plant scientists. In addition, reliably detecting crop stand in-field and in real-time can enable a range of precision agriculture applications and lead to new inventions in agricultural field automation such as robotic weed control. This invention is concerned with a novel sensing approach of detecting, counting, and analyzing crop seedlings by using reflective laser proximity sensors. The laser sensors used in this invention are different than the sensors used in any other existing approaches. These sensors are based on reflected laser light beam technology and can suppress background noise. Compared with other through-beam types of sensors, the reflective laser proximity sensors offer a great advantage in its ease of use in field deployment. The reflective laser proximity sensors suppress background noise. Note that the use of reflective laser proximity sensors may be advantageous relative to other types of sensors in various ways including ease of deployment in the field, a fast response time (e.g. 250-750 micro-seconds) and lower cost. Their cut-off sensing range is also adjustable so that they will not react to the plants beyond the targeted crop row. Multiple laser sensors may be vertically lined up to form a sensor bank or a sensor array and their positions are changeable based on the height of crop stands. This sensor bank may be carried by a mobile platform, e.g., a cart or a vehicle. With the sensor bank being set up perpendicular to the ground surface, the mobile platform may push the sensor bank alongside of a crop row to scan crop seedlings. When there is a plant object within the sensing range in front of a sensor, an On (high voltage) signal will be generated, otherwise an Off (low voltage) signal will be generated by the sensor. These On/Off switch signals generated by the sensors will be tagged by a distance marker generated by a travel distance sensor, e.g., a wheel shaft encoder. In this way, a sensor signal map which represents the profile of the side-view of the crop row will be generated. Through processing this crop row profile by a customized computer algorithm, crop stand can be detected. In the meantime, the interplant spacing and crop stand thickness can be estimated. If GPS (Global Positioning System) position signal is provided to the system, the system can then geo-reference each crop stand and thus creating a crop stand distribution map in the field.

Figure 1:
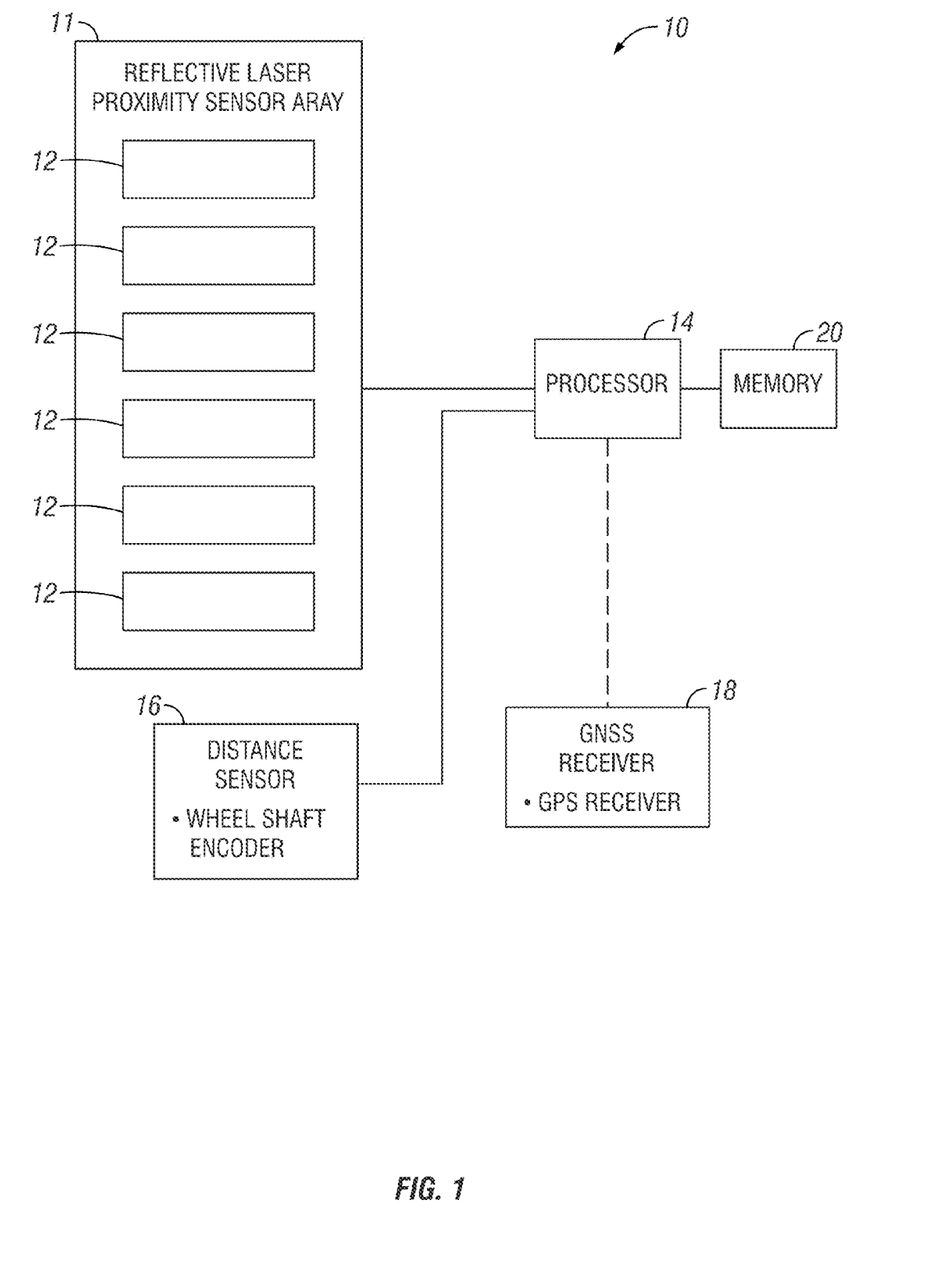
FIG. 1 illustrates a block diagram of one example of a crop stand analyzer.

FIG. 1 is a block diagram of one example of a crop stand analyzer. As shown in FIG. 1, a crop stand analyzer 10 includes a reflective laser proximity sensor array 11 with a plurality of reflective laser proximity sensors 12. The reflective laser proximity sensors 12 of the array 11 are operatively connected to a processor 14. A distance sensor 16 which may be a wheel shaft encoder is also operatively connected to the processor 14. A global navigation satellite system (GNSS) such as a Global Positioning System (GPS) receiver may be operatively connected to the processor 14 as well. Location information may be used to geo-reference each crop stand so that a crop stand distribution map may be created for a field area. A non-transitory machine readable memory 20 may also be operatively connected to the processor 14.

A plurality of vertically aligned reflective laser proximity sensors 12 form a sensor bank or sensor array 11 which extends perpendicularly and upward from the ground surface. The height at which the laser sensors 12 are placed may be adjusted based on the height of the crop stand being analyzed. The sensors 12 within the sensor bank 11 may be used simultaneously such that at any location the presence or absence of a plant object can be detected as well as the height of the plant object. A distance marker generated by the travel distance sensor 16 (e.g. a wheel shaft encoder) may be used to tag each set of laser sensor measurements. Thus, as the crop stand analyzer 10 is moved along a crop row, sufficient information is acquired to construct a profile of the side-view of the crop row. By processing of the crop row profile the crop stand can be detected. Moreover, the interplant spacing and crop stand thickness may be estimated.

Figure 2:
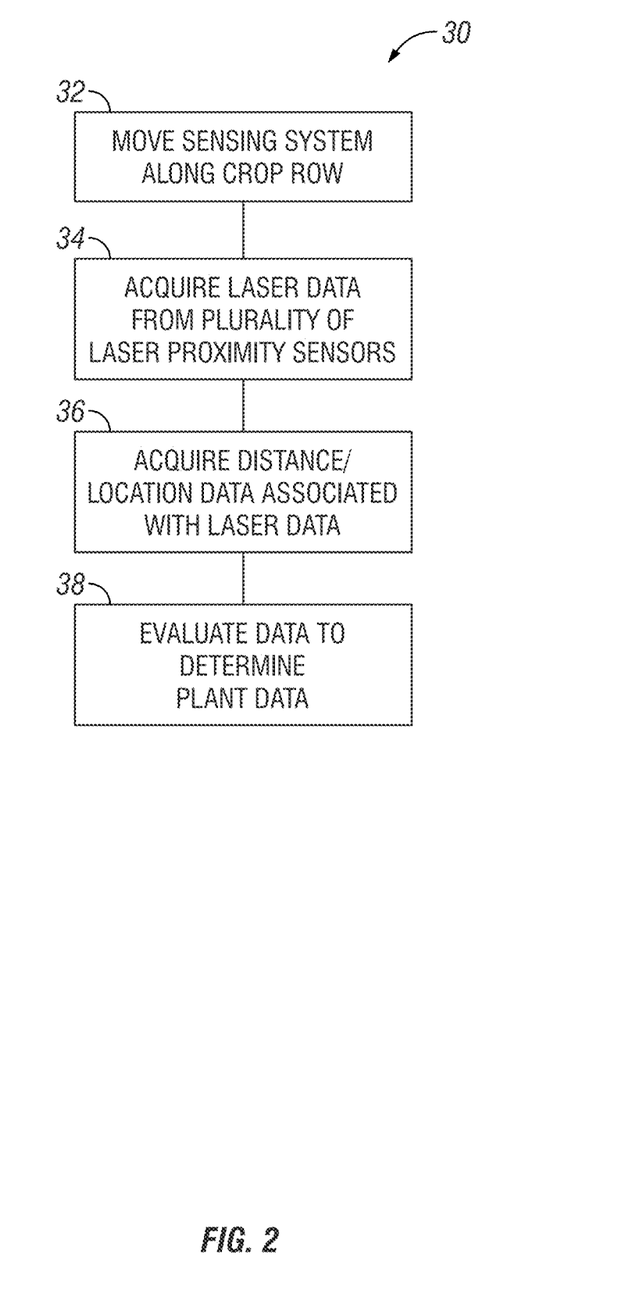
FIG. 2 illustrates a flow diagram of one example of a method associated with a crop stand analyzer.

In operation, as shown in the method 30 of FIG. 2, the sensing system associated with the crop stand analyzer moves along a crop row in step 32. As the sensing system of the crop stand analyzer moves along the row, laser data is acquired from the plurality of laser proximity sensors in step 34. In step 36, distance/location data associated with the laser data is also acquired. This may include data from a distance sensor and may also include data from a Global Navigation Satellite System (GNSS) receiver. Thus, this distance/location data may be associated with or otherwise referenced to the laser data. In step 38, the collected data may be evaluated to determine plant data.

Figure 3:
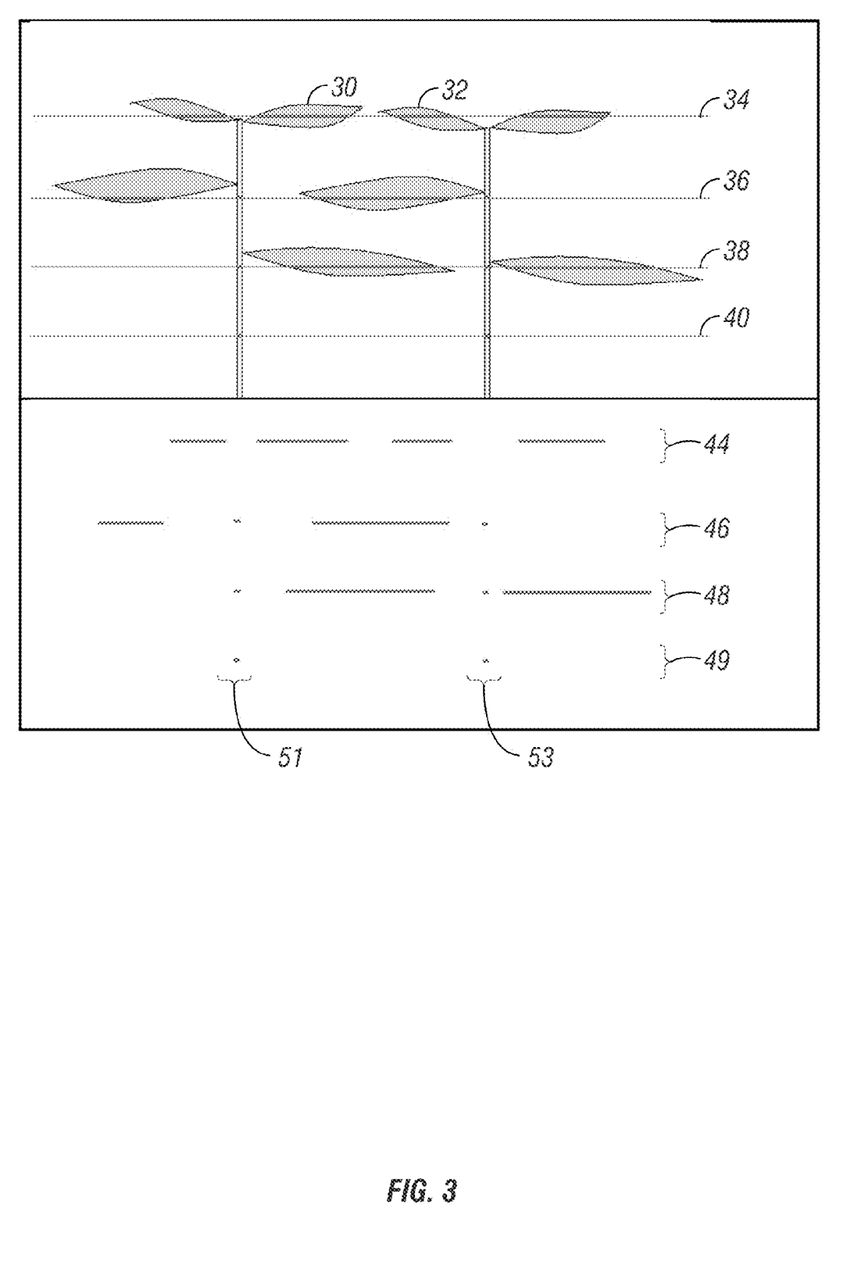
FIG. 3 is an illustration of how a crop row sensor signal map may be generated.

FIG. 3 illustrates how a crop row sensor signal map may be generated. As shown in FIG. 3, plants 30, 32 are adjacent plants within the same row. Lines 34, 36, 38, 40 illustrate different vertical distances from the ground surface or heights. There may be a different reflective laser proximity sensor for each of these different heights. Below the plants rows of horizontal line segments 44, 46, 48, 49 correspond with lines 34, 36, 38, 40, respectively, to form a crop row sensor signal map. Thus, the crop row signal may be interpreted to define to plants as there are two sets 51, 53 of vertically aligned horizontal segments. When the crop row sensor signal map is referenced to distance information, the distance between the sets 51, 53 (representing stems) may be calculated to show the distance between plants. Other information potentially includes height information based on the height of the sensors, the presence, location of, and size information for leaves.

Figure 4:
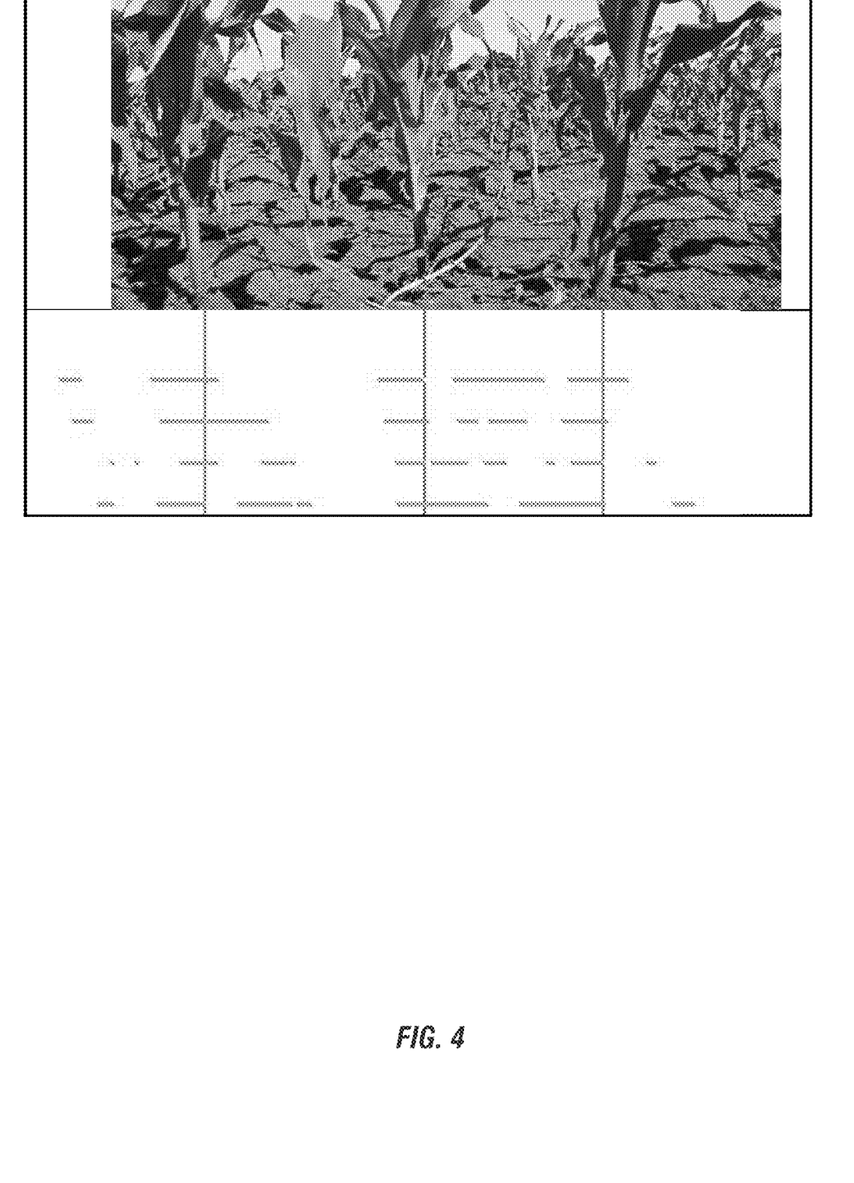
FIG. 4 is an example of a real signal map generated by corn plants in an experimental field.

FIG. 4 illustrates an example of a real signal map generated by corn plants in an experimental field. The horizontal line segments represent sensor response to corn plant seedlings. The vertical lines represented detected corn plant stands.

Figure 5A:
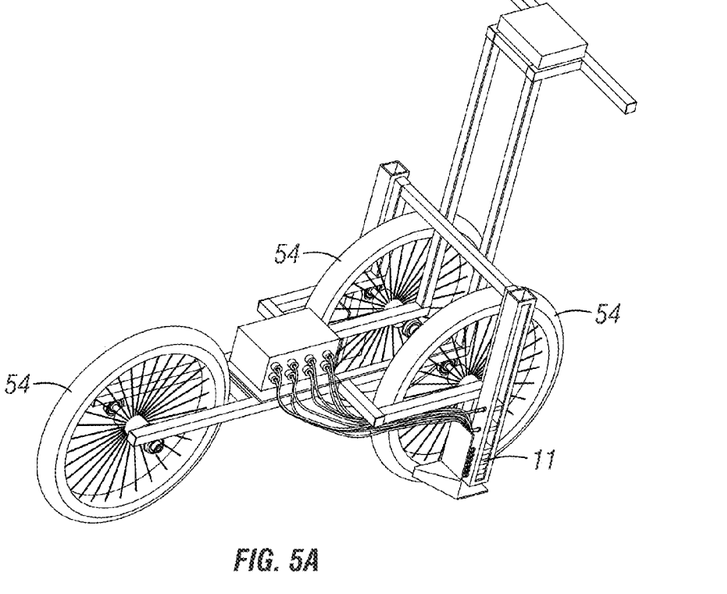
FIGS. 5A-5C illustrate one example of a crop stand analyzer with a mobile platform.
Figure 5B:
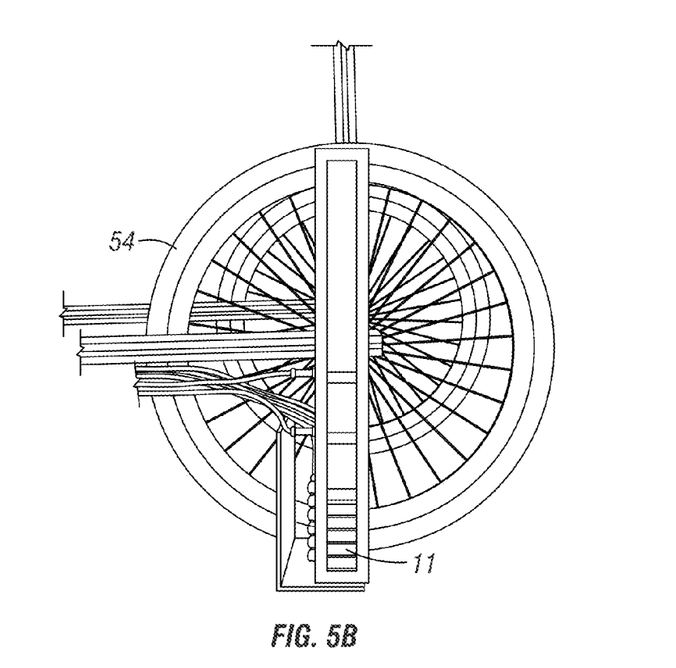
Figure 5C:
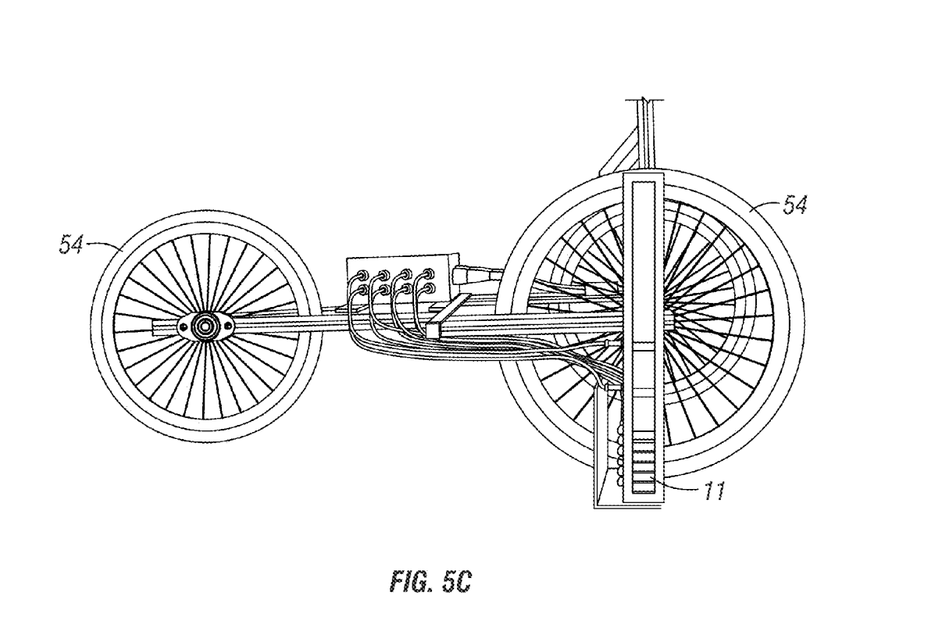

FIG. 5A-5C illustrate one example of a crop stand analyzer with a mobile platform. This proof of concept prototype was built on top of a baby jogger, where two sensor banks are installed on the left and right sides and a wheel encoder is mounted on the front axle. A protection shield with an open slot in the middle is placed in front of the sensor bank. There are eight laser sensors installed in each sensor bank. This unit can sense two crop rows at the same time.

Figure 6A:
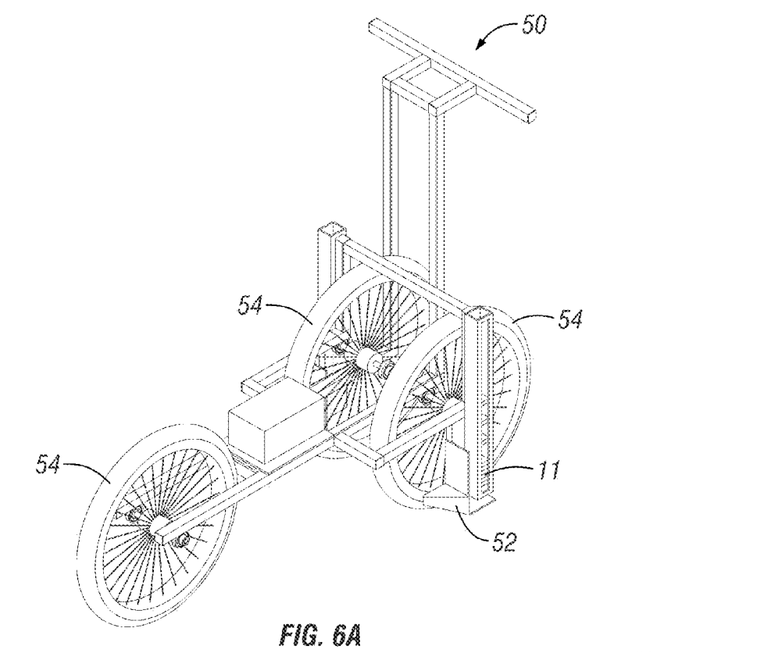
FIGS. 6A-6B illustrate an example of a crop stand analyzer with a cart type sensing system.
Figure 6B:
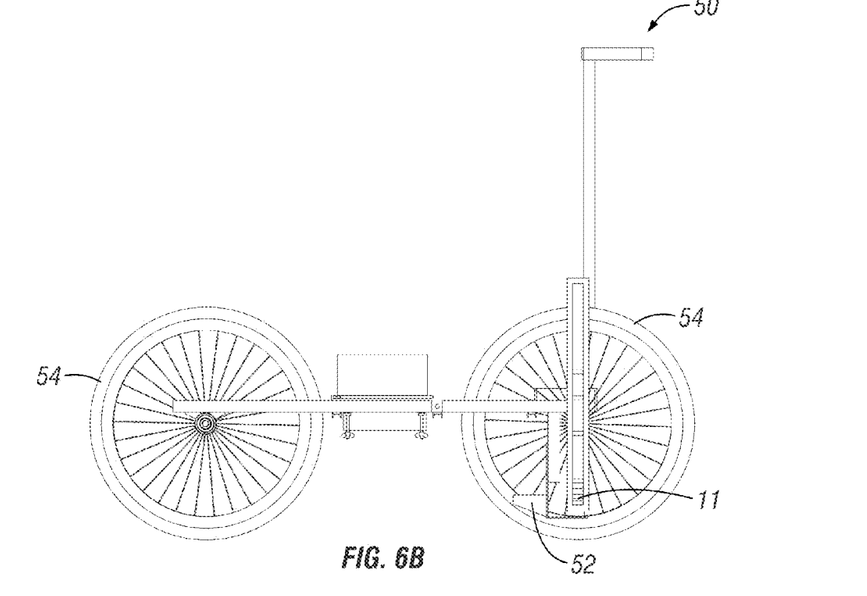

FIG. 6A and FIG. 6B illustrate an improved design of the cart type sensing system 50 where sensor banks 11 are mounted vertically at the wheel shaft location. This assists the sensor banks 11 to contour uneven soil surfaces. A protection shield 52 is added to the front of the sensor bank 11 in the direction of travel. Here, larger wheels 54 (20 inch diameter) are used to gain smoother travel in the field.

Figure 7:
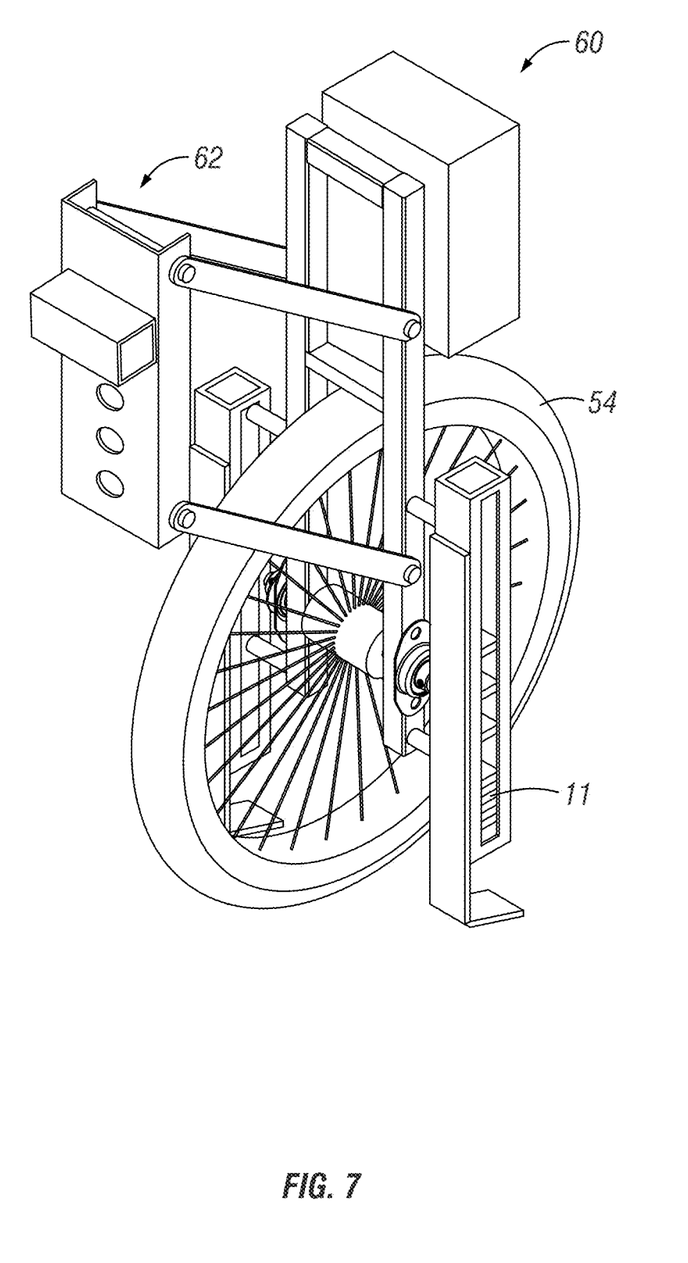
FIG. 7 illustrates an example of a vehicle mount row-unit with a sensing system.

FIG. 7 illustrates another example of a sensing system which may be used on any number of types of vehicles or other mobile platforms, including tractors, all-terrain vehicles, high-ground clearance sprayers, and other types of vehicles. The row unit system 60 uses a uni-wheel supported double-sensor bank design so that it may be pulled between two crop rows and analyze two row crop stands simultaneously. A parallel 4-bar linkage 62 may be used to allow vertical movement of the sensor-wheel assembly. A tensioned spring (not shown) may be used inside the 4-bar linkage 62 to generate down-force to keep the wheel on the ground.

Figure 8A:
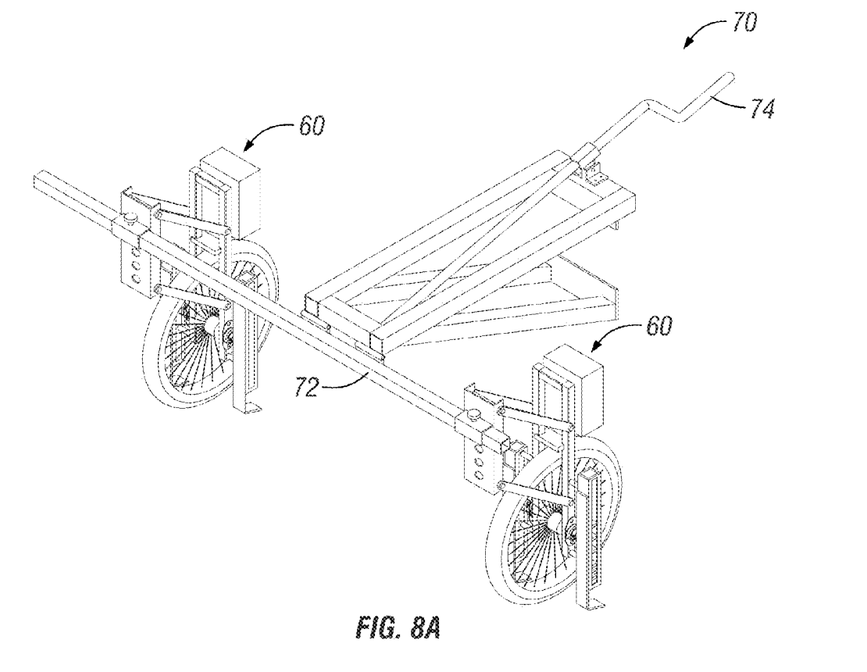
FIGS. 8A-8B illustrate an example of an all-terrain vehicle mount for mounting multiple row-units on a toolbar.
Figure 8B:
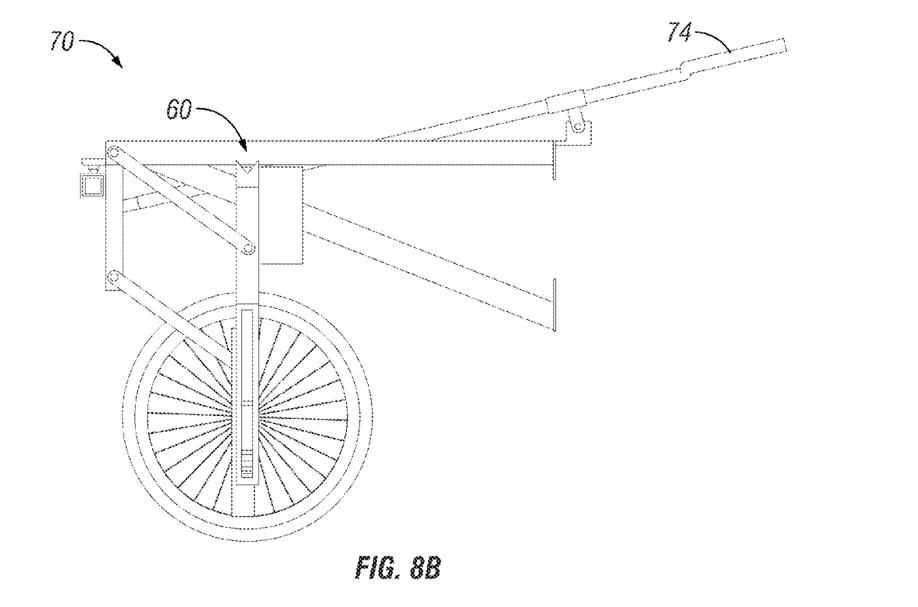
Figure 9A:
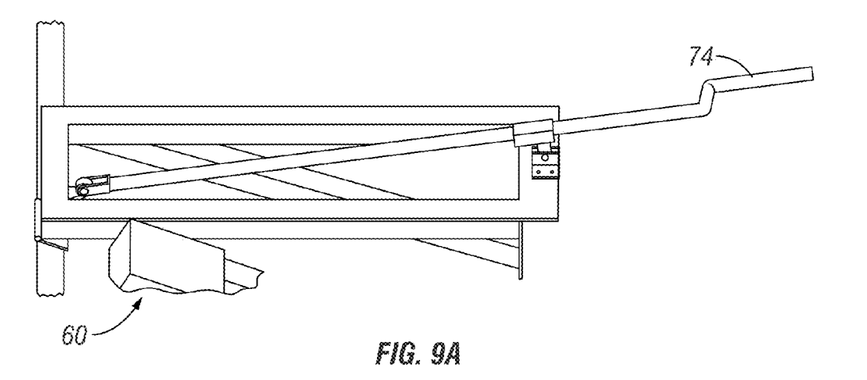
FIGS. 9A-9B illustrate an example of how a crank can rotate the toolbar and lift the row-units up.
Figure 9B:
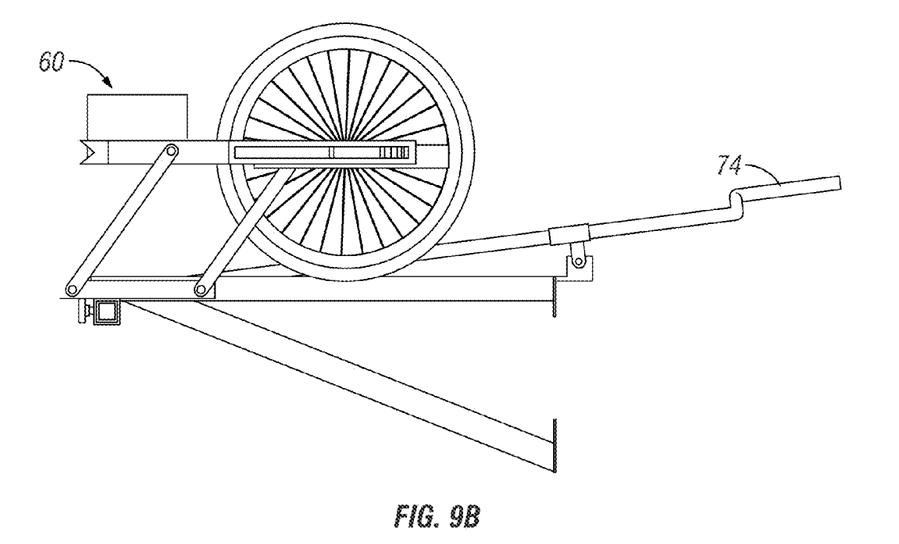

FIG. 8A and FIG. 8B illustrate one example of an all-terrain vehicle (ATV) mount 70. Two row-units 60 may be mounted on a toolbar 72 in front of an ATV. A crank 74 may be used to rotate the toolbar so that the row units 60 will be lifted off the ground for turning in headlands and for transportation on a road. FIG. 9A and FIG. 9B further illustrate how the crank 74 may be used to rotate the toolbar and lift the row-units up.

Figure 10:
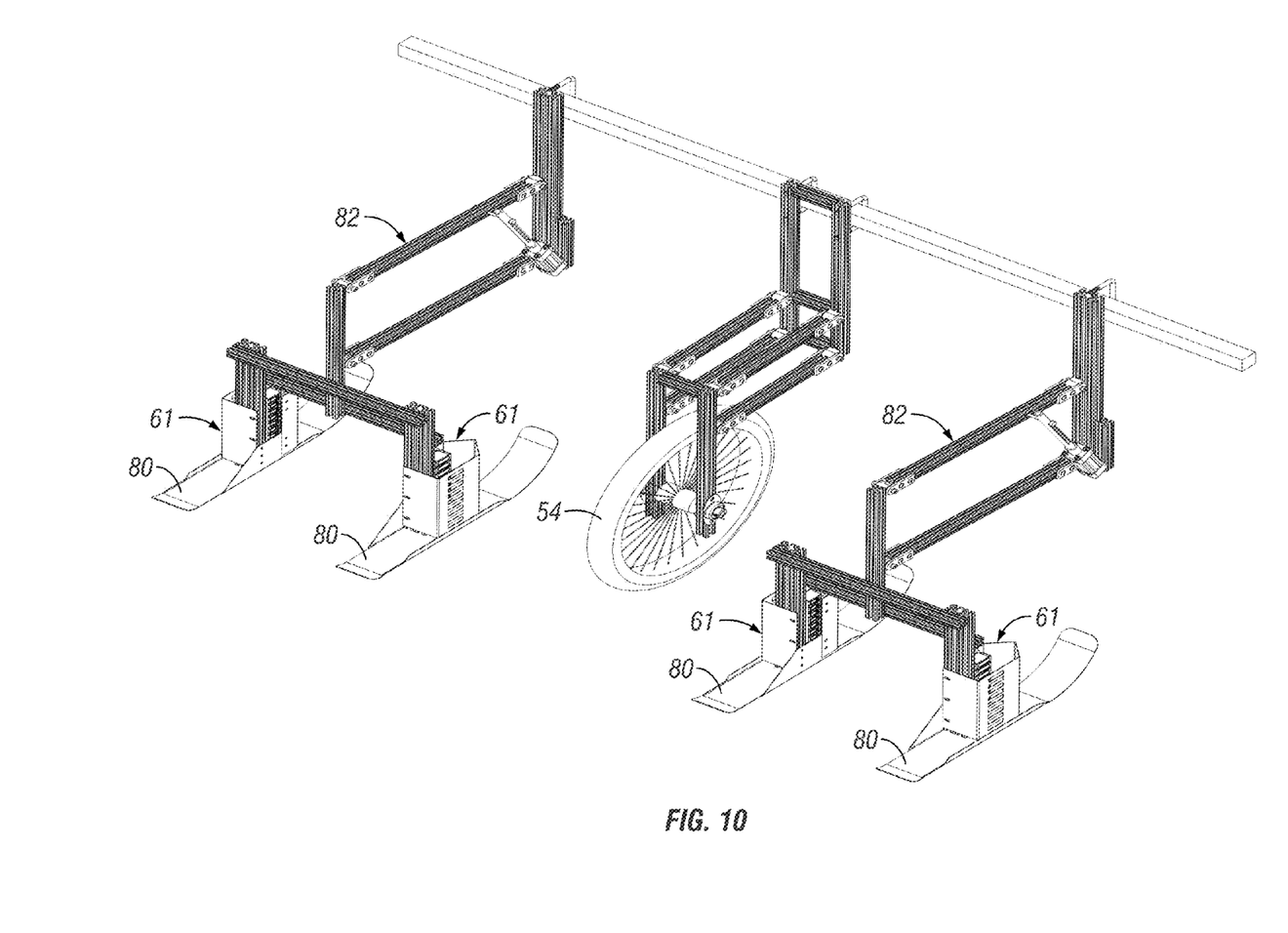
FIG. 10 illustrates an example of a 2-to-1 configuration where row units are connected together and attached to one 4-bar linkage. For each crop row, sensors are mounted on to a sled to glide on soil surfaces and are housed in a shield with sensor view windows.

FIG. 10 illustrates a 2-to-1 configuration where two row units are connected together and attached to one 4-bar linkage 82. This gives more compact design and reduces the number of 4-bar linkages for sensor banks by half. As shown in FIG. 10 each row unit is associated with a sled 80 and a single wheel 54 is shown. A controller box (not shown) may also be present for each row unit. A sensor shroud or sensor protector with sensor view windows 61 is also shown.

Figure 11:
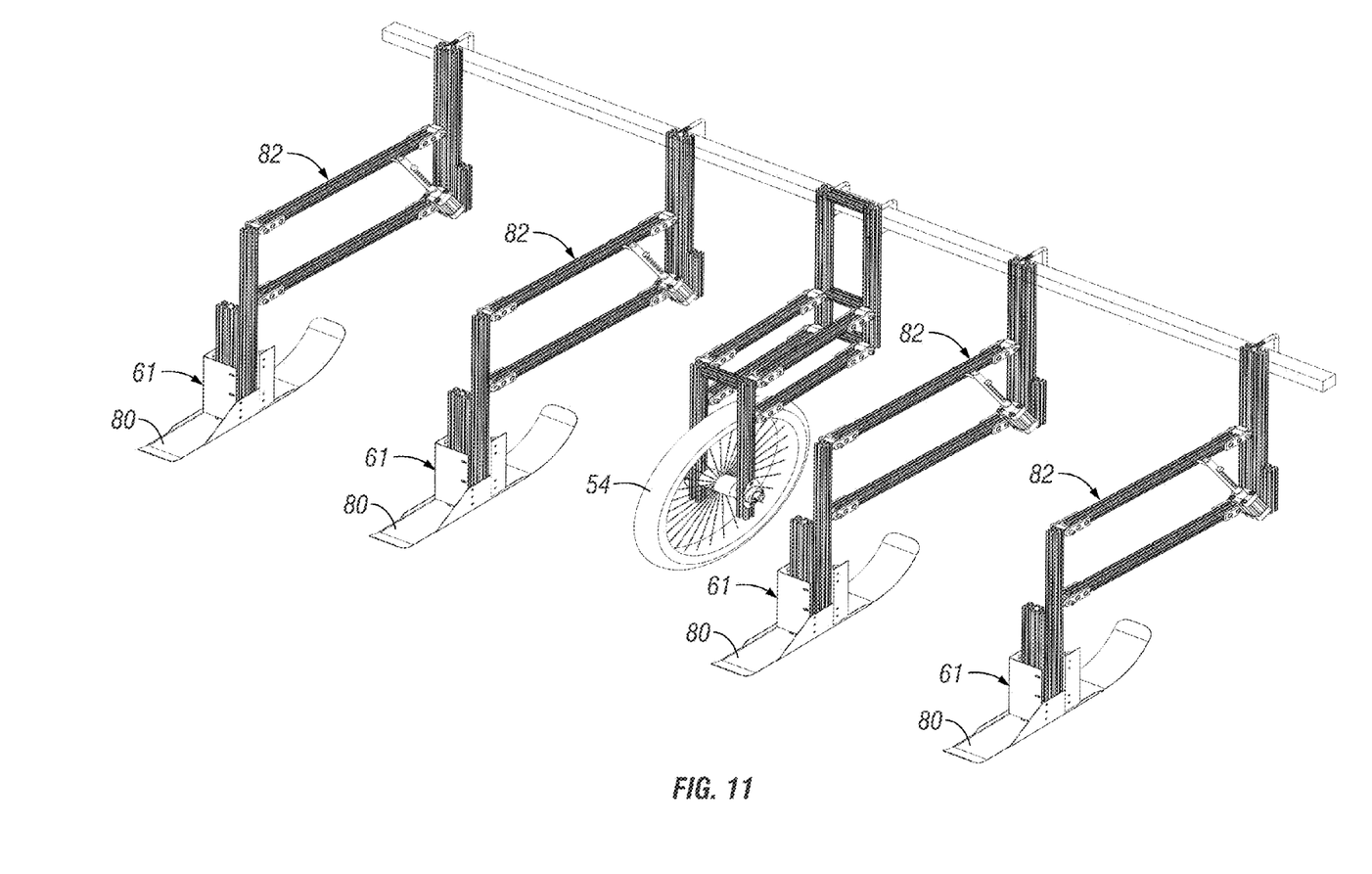
FIG. 11 illustrates an example of a 1-to-1 configuration where every row unit is attached to one 4-bar linkage.

FIG. 11 illustrates a 1-to-1 configuration where every row unit is attached to one 4-bar linkage 82. This configuration gives better adaptability to uneven soil surfaces between the rows.

It should be appreciated that the system described may be used to detect various types of plant information including plant population, interplant spacing, stem diameter, and tiller.

Plant population—Plant population can be calculated directly by counting each plant within a field area. Plant population may also be estimated based on the number of rows within a field area and the number of plants within the row. Plant population may be estimated based on the width of the row, the length of the row, and the number of plants per row, or the number of plants per a given length of the row.

Interplant spacing—Interplant spacing is the spacing between adjacent plants. The crop stand analyzer provides for determining the location of each plant object and referencing the location to a distance (such as provided by the distance sensor). Thus the difference in location between adjacent plants can be readily calculated as the difference between their positions.

Stem diameter—The crop stand analyzer provides for determining the presence or absence of a plant object thus, the stem diameter of a given plant object may be determined from the distance at which the plant is first detected and when it is last detected.

Tillers—The crop stand analyzer can distinguish tillers as long as they are viewable by the sensors.

In addition to plant parameters such as those described above, it is contemplated that other plant parameters related to the size, shape, position, or number of plants may also be measured or estimated from information provided by the laser sensors.

The collected information may be used in numerous ways. One use of the collected information is in plant breeding programs. The collected information includes plant phenotype information which may be important in evaluating a particular type, hybrid, or variety of plant and determining whether or not the particular type should be used within a plant breeding program or selected for commercialization. Another use of the collected information is in precision agriculture applications. For example, collected information may be used in determining the type or amount of chemicals to be applied to the plants or soil as a part of an automated system for variable rate applications or the information may be used in precision weeding applications. The collected information may also be used to assist in replanting, variable seeding, fertilization, and other applications. Of course, other uses are also contemplated.

Therefore, various methods, systems, and apparatuses for crop stand analysis have been disclosed. The present invention is not to be limited to the specific examples provided herein as numerous variations, options, and alternatives are contemplated. For example, variations in the manner of conveying the crop stand analyzer through a field are contemplated as are variations in the number and placement of sensors, the manner in which sensor information is processed, and other variations.

What is claimed is:

1. A crop stand analyzer comprising:
   a first plurality of reflective laser proximity sensors, the reflective laser proximity sensors arranged in a vertical row and perpendicularly to a ground surface to detect plant objects;
   a distance sensor;
   a processor operatively connected to the first plurality of reflective laser proximity sensors and the distance sensor;
   wherein the crop stand analyzer is configured to generate side-view profiles for the plant objects and then extract plant stand information via these profiles.

2. The crop stand analyzer of claim 1 wherein the distance sensor comprises a wheel shaft encoder.

3. The crop stand analyzer of claim 2 further comprising a mobile platform, the first plurality of reflective laser proximity sensors mounted to the mobile platform and a wheel associated with the wheel shaft encoder operatively connected to the mobile platform.

4. The crop stand analyzer of claim 3 wherein the mobile platform comprise a cart.

5. The crop stand analyzer of claim 1 wherein the plant stand information comprises population, interplant spacing and stem diameter.

6. The crop stand analyzer of claim 1 wherein the processor is configured to reference data from the reflective laser proximity sensors to data from the distance sensor.

7. The crop stand analyzer of claim 1 further comprising a global navigation satellite system receiver operatively connected to the processor.

8. The crop stand analyzer of claim 7 wherein the processor is configured to reference data from the distance sensor to position data from the global navigation satellite system receiver.

9. The crop stand analyzer of claim 1 further comprising a second plurality of reflective laser proximity sensors arranged in a vertical row and perpendicularly to a the ground surface to detect plant objects and wherein the first plurality of reflective laser proximity sensors detect plant objects in a first row and the second plurality of reflective laser proximity sensors detect plant objects in a second row.

10. An agricultural vehicle comprising the crop stand analyzer of claim 1.

11. An agricultural vehicle comprising a plurality of the crop stand analyzer of claim 1.

12. A method for analyzing crop stands, comprising steps of:
providing a system comprising (a) a first plurality of reflective laser proximity sensors, the reflective laser proximity sensors arranged in a vertical row and perpendicularly to a ground surface to detect plant objects, (b) a distance sensor, and (c) a processor operatively connected to the first plurality of reflective laser proximity sensors and the distance sensor;
acquiring laser data from the first plurality of reflective laser proximity sensors;
acquiring position data from the distance sensor;
registering the position data with the laser data using the processor;
computing plant data comprising at least one of plant population data, interplant spacing, and stem spacing from the position data and the laser data.

13. The method of claim 12 wherein the steps of acquiring the laser data, acquiring the position data, registering the position data with the laser data, and computing the plant data is performed as the system is moved through a field.

14. The method of claim 12 further comprising determining whether to advance a hybrid or variety in a plant breeding program using the plant data.

15. The method of claim 12 further comprising determining whether to commercialize a hybrid or variety using the plant data.

16. A crop stand analyzer comprising:
a plurality of row units wherein each of the row units comprises (a) a first plurality of reflective laser proximity sensors, the reflective laser proximity sensors arranged in a vertical row and perpendicularly to a ground surface to detect plant objects, (b) a distance sensor;
a processor operatively connected to each of the first plurality of reflective laser proximity sensors and each of the distance sensors;
wherein the processor is configured to generate side-view profiles for the plant objects and then extract plant stand information via these profiles.

17. The crop stand analyzer of claim 16 further comprising a mobile platform, each of the first plurality of reflective laser proximity sensors mounted to the mobile platform and at least one wheel operatively connected to the mobile platform.

\* \* \* \* \*